United States Patent [19]

Harris et al.

[11] Patent Number: 5,210,216

[45] Date of Patent: May 11, 1993

[54] CALIXARENE AND OXACALIXARENE DERIVATIVES AND USE THEREOF OF SEQUESTRATION METALS

[75] Inventors: Stephen J. Harris, Dublin; John Guthrie, County Kildare; Maureen MacManus; Ciaran McArdle, both of Dublin, all of Ireland; Michael A. McKervey, Belfast, Northern Ireland

[73] Assignee: Loctite (Ireland) Limited, Dublin, Ireland

[21] Appl. No.: 625,573

[22] Filed: Dec. 10, 1990

Related U.S. Application Data

[63] Continuation-in-part of Ser. No. 248,874, Sep. 23, 1988, Pat. No. 5,043,415, which is a continuation-in-part of Ser. No. 20,918, Mar. 2, 1987, Pat. No. 4,882,449, and a continuation-in-part of Ser. No. 145,993, Jan. 20, 1988, Pat. No. 4,855,461, and a continuation-in-part of Ser. No. 100,494, Sep. 24, 1987, abandoned, which is a continuation-in-part of Ser. No. 870,677, Jun. 4, 1986, Pat. No. 4,699,966, which is a continuation-in-part of Ser. No. 717,251, Mar. 28, 1985, Pat. No. 4,642,362, said Ser. No. 20,918, is a continuation-in-part of Ser. No. 870,677, Jun. 4, 1986, Pat. No. 4,699,966, and a continuation-in-part of Ser. No. 825,012, Jan. 31, 1986, Pat. No. 4,695,615, which is a continuation-in-part of Ser. No. 145,993, Jan. 31, 1986, and Ser. No. 717,251, Jan. 31, 1986.

[30] Foreign Application Priority Data

Dec. 13, 1989 [IE] Ireland ............................ 3982/89

[51] Int. Cl.$^5$ .................. C07D 207/08; C07D 313/00
[52] U.S. Cl. ........................ 548/518; 549/346; 549/347; 549/352; 549/353; 564/36; 564/74; 564/251; 564/265; 564/305; 564/306; 568/66; 568/33
[58] Field of Search ............ 549/348, 354, 397, 347, 549/352, 353; 568/325, 633, 66, 33; 548/571, 518; 564/36, 74, 251, 265

[56] References Cited

U.S. PATENT DOCUMENTS

| | | | |
|---|---|---|---|
| 4,622,414 | 11/1986 | McKervey | 568/325 |
| 4,642,362 | 2/1987 | Harris et al. | 516/419 |
| 4,699,966 | 10/1987 | Harris et al. | 528/12 |
| 4,718,966 | 1/1988 | Harris et al. | 568/633 |
| 4,855,461 | 8/1989 | Harris | 549/348 |
| 4,866,198 | 9/1989 | Harris | 568/325 |
| 4,882,449 | 11/1989 | Harris | 568/325 |
| 4,908,399 | 3/1990 | Harris et al. | 524/243 |
| 4,933,407 | 6/1990 | Harris et al. | 549/348 |
| 5,043,415 | 8/1991 | Harris et al. | 549/348 |

FOREIGN PATENT DOCUMENTS

| | | |
|---|---|---|
| 0309291 | 3/1989 | European Pat. Off. |
| 62-136242 | 6/1987 | Japan |
| 62-223156 | 10/1987 | Japan |
| 62-265250 | 11/1987 | Japan |
| 63-007837 | 1/1988 | Japan |
| 63-099035 | 4/1988 | Japan |

Primary Examiner—C. Warren Ivy
Assistant Examiner—A. A. Owens
Attorney, Agent, or Firm—Edward K. Welch, II; Eugene F. Miller

[57] ABSTRACT

Calixarene and oxacalixarene derivatives of the formula IV:

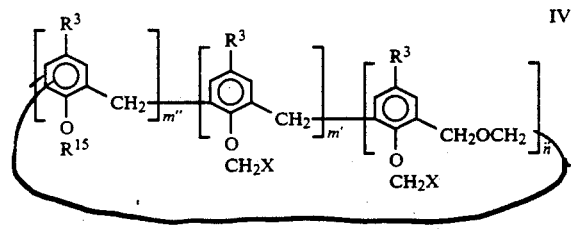

wherein
$m' + m'' = 0-8$
$n = 0-8$
$m' \geq \frac{1}{2}(m' + m'')$
$3 \leq m' + m'' + n \leq 8$
if $n = 0$, $m' + m'' \geq 4$ $R^3$ is H, halogen, or hydrocarbyl, aryl, hydrocarbylaryl or a substituted derivative thereof and $R^3$ may be the same or different on each aryl group;

$R^{15}$ is H or hydrocarbyl, aryl, hydrocarbylaryl or a substituted derivative thereof;

X is selected from

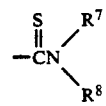 (A)

−(CH₂)ₙ'SR⁷ (B)

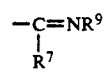 (C)

-continued

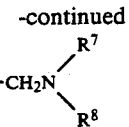 (D)

wherein $R^7$ and $R^8$ which may be the same or different are H or hydrocarbyl (including a cycloaliphatic ring formed by $R^7$ and $R^8$ together), aryl, hydrocarbylaryl or a substituted derivative thereof; $R^9$ is —OH, —NH₂, —NHC(O)NH₂ or —NHAr, wherein Ar is aryl or a substituted derivative thereof, n' is 0 or 1.

Use of the compounds for sequestration of metals is also described.

8 Claims, No Drawings

CALIXARENE AND OXACALIXARENE DERIVATIVES AND USE THEREOF OF SEQUESTRATION METALS

This application is a continuation-in-part of Ser. No. 248,874, Sept. 23, 1988, U.S. Pat. No. 5,043,415, which is a continuation-in-part of Ser. No. 20,918, Mar. 2, 1987, U.S. Pat. No. 4,882,449, Ser. No. 145,993, Jan. 20, 1988, U.S. Pat. No. 4,855,461, and Ser. No. 100,494, Sep. 24, 1987, abandoned, which is a continuation-in-part of Ser. No. 870,677, Jun. 4, 1986, U.S. Pat. No. 4,699,966, which is a continuation-in-part of Ser. No. 717,251, Mar. 28, 1985, U.S. Pat. No. 4,642,362, said Ser. No. 20,918, is a continuation-in-part of Ser. No. 870,677, and Ser. No. 825, 012, Jan. 31, 1986, U.S. Pat. No. 4,695,615, which is a continuation-in-part of Ser. No. 145,993, and Ser. No. 717,251.

CROSS REFERENCE TO RELATED APPLICATION

This application is related to application Ser. No. 625,575, filed on Dec. 10, 1990, entitled "Polymerisable Calixarene and Oxacalixarene Derivatives, Polymers thereof and use of such Derivatives and Polymers for Sequestration of Metals".

BACKGROUND OF THE INVENTION a) Field of the Invention

This invention relates to novel calixarene derivatives and to the use of such derivatives for sequestration of metals.

b) Description of the Related Art

U.S. Pat. No. 4,882,449 Harris et. al. describes nitrogen-containing calixarene derivatives selected from the groups represented by the formulae I and II:

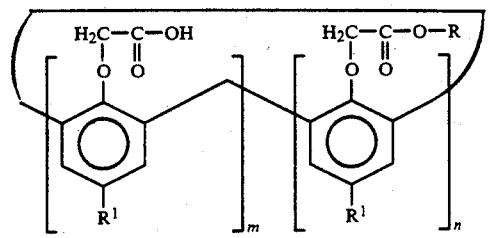

I

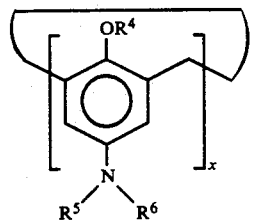

II wherein
m+n=4, 6 or 8
n=an integer 1-8
m=an integer 0-7
x=4, 6 or 8
$R^1$ is H, alkyl, aralkyl, alkoxy, aroyl, or alkoyl,
R is aliphatic or aromatic, unsubstituted or substituted, hydrocarbyl containing nitrogen.
$R^4$ is unsubstituted or substituted hydrocarbyl, carbonyl or aryl;
$R^5$ and $R^6$ (which may be the same or different) are hydrogen, or unsubstituted or substituted hydrocarbyl.

That application also describes use of such calixarene derivatives for selectively sequestering transition metals from aqueous mixtures of alkali metals and transition metals.

European Patent Publication No. 0,309,291 (Application No. 88 308 897.3) describes oxacalixarene and calixarene derivatives of the formula III:

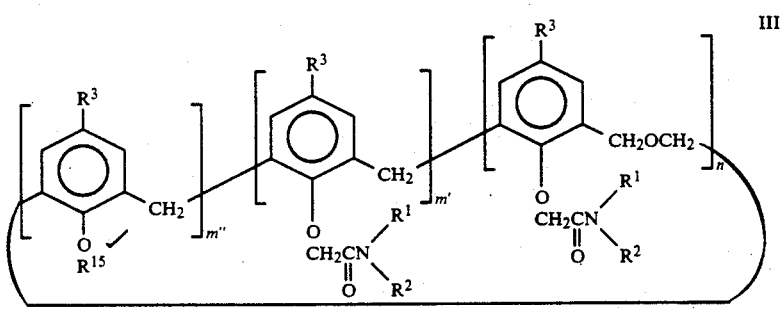

III wherein
m'+m"=0-8
n=0-8
m'≧½ (m'+m")
3≦m'+m"+n≦8
if n=0, m'+m"≧4
$R^3$ is H, halogen, or hydrocarbyl, aryl, hydrocarbylaryl or a substituted derivative thereof and $R^3$ may be the same or different on each aryl group;
$R^1$ and $R^{15}$ which may be the same or different are H or hydrocarbyl, aryl, hydrocarbylaryl or a substituted derivative thereof;
$R^2$ is selected from:
$R^4$ which is H, or hydrocarbyl, aryl, hydrocarbylaryl or a substituted derivative thereof,

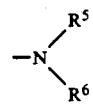

wherein $R^5$ and $R^6$ which may be the same or different are H, hydrocarbyl, aryl, hydrocarbylaryl, or a substituted derivative thereof, —$OR^1$, wherein $R^1$ is as defined above, and $R^{17}$ which is a residue of a hydrocarbyl, aryl or hydrocarbylaryl group or of a substituted derivative thereof providing a bond to another oxacalixarene or calixarene derivative of formula III wherein $R^2$ is $R^{17}$.

That application also describes use of such compounds for sequestering transition metals such as copper and silver, transition series elements such as manganese, alkaline earth elements such as calcium and magnesium, and Group III elements such as aluminium in addition to alkali metals. However the compounds described therein are not selective in their action in sequestering the said metals and other elements.

U.S. Pat. No. 4,477,377 Izatt et. al., describes the use of calix(8)arene, calix(6)arene or calix(4)arene in selective recovery of cesium ions from mixtures thereof with other metals, particularly alkali metals.

Other nitrogen-containing calixarene derivatives are described by C.D. Gutsche and K.C. Nam in J. Am. Chem. Soc., 1988 110 pages 6153-62.

SUMMARY OF THE INVENTION

The present inventors have now prepared novel calixarene and oxacalixarene derivatives which have unexpected sequestration properties and/or other useful properties.

The present invention provides novel calixarene and oxacalixarene derivatives of the formula IV:

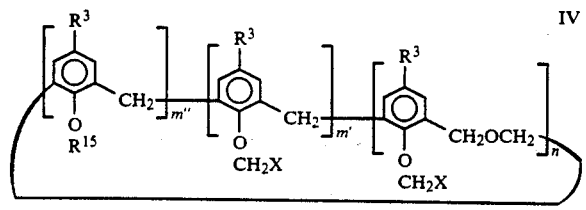

wherein
m'+m''=0-8
n=0-8
m'≧⅓ (m'+m'')
3≦m'+m''+n≦8
if n=0, m'+m''≧4

$R^3$ is H, halogen, or hydrocarbyl, aryl, hydrocarbylaryl or a substituted derivative thereof and $R^3$ may be the same or different on each aryl group;
$R^{15}$ is H or hydrocarbyl, aryl, hydrocarbylaryl or a substituted derivative thereof;
X is selected from

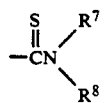 (A)

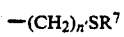 (B)

 (C)

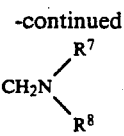 (D)

wherein $R^7$ and $R^8$ which may be the same or different are H or hydrocarbyl (including a cycloaliphatic ring formed by $R^7$ and $R^8$ together), aryl, hydrocarbylaryl or a substituted derivative thereof; $R^9$ is —OH, —$NH_2$, —NHC(O)$NH_2$ or —NHAr, wherein Ar is aryl or a substituted derivative thereof, n' is 0 or 1.

Compounds of formula IVA have been found to be capable of preferentially sequestering heavy/precious metals over alkali metals and alkaline earths. They are therefore capable of removing heavy/precious metals from aqueous mixtures of such metals with alkali metals and/or alkaline earths. When bound to a carrier such as a polymer or silicon dioxide they will have utility for removal of toxic heavy metals such as cadmium, lead or silver from water, particularly drinking water, without removing beneficial alkali metals such as calcium and sodium. Compounds of formula IVB have been found to be capable of preferentially sequestering silver and gold over transition metals such as copper and alkali metals such as sodium. They are therefore capable of removing silver or gold from an aqueous mixture thereof with alkali metals, or from an aqueous mixture thereof with transition metals. They will have utility in extraction of precious metals from sea water and for recovery of silver in the photographic industry. Compounds of formula IVC have been found to be capable of sequestering precious/transition metals such as copper and silver, alkaline earths such as calcium, heavy metals such as lead and cadimum and lanthanides such as ytterbium. Compounds of formula IVD have been found to be capable of sequestering a wide range of metals including alkali metals, alkaline earths, transition metals, heavy and precious metals and lanthanides.

In one aspect, the present invention provides a method of sequestering metals which comprises contacting a metal-containing medium with a calixarene or oxacalixarene derivative of formula IV as defined above.

The term "hydrocarbyl" as used herein means aliphatic hydrocarbyl including alkyl, alkenyl and alkynyl and also includes alkylene and alkenylene groups in the case where $R^7$ and $R^8$ together form a cycloaliphatic ring. Hydrocarbyl groups shall preferably contain from 1 to 10 carbon atoms, more preferably from 1 to 5 carbon atoms, and aryl and hydrocarbylaryl groups shall preferably have from 6 to 20 carbon atoms, more preferably from 6 to 10 carbon atoms. Hydrocarbyl groups are preferred, especially alkyl or alkenyl groups. A substituted derivative of the foregoing may suitably be substituted with one or more halo groups or substituted or interrupted by one or more oxo groups. Halogen may be chlorine, bromine, fluorine or iodine.

The preferred calixarene or oxacalixarene derivatives of formula IV are those in which m''=0 or 1, m'=6, 4 or 3, n=0, 1 or 2. Preferably m''+m'+n=4 or 6.

The preparation of calixarene derivatives is known and is described, for example, in C. Gutsche et. al., Acc. Chem. Res., 16, 161-170 (1983); in U.S. Pat. No. 4,556,700 Harris et. al., and in J. Inclusion Phenomena 2

199-206 (1984) D. Reidel Publishing Company; the appropriate disclosures of all of which are incorporated herein by reference.

The preparation of aryl calixarene derivatives is described in European Patent Application No. 87 306 963.7 and equivalent applications in other countries.

Mixed functionality calixarene derivatives are described in European Patent Application No. 0,196,895 A2 and U.S. Pat. No. 4,642,362 Harris et. al. When m" is greater than or equal to 2 in the compounds of formula IV, the aryl groups having the $-O-R^{15}$ side chain may be interspersed around the ring between the aryl groups having the $-OCH_2X$ side chain.

In the oxacalixarene derivatives of formula IV when (m'+m") and n are greater than 2, the methylene and ether bridges may or may not alternate within the oxacalixarene molecule.

Oxacalixarene compounds may be readily synthesised by methods described in C. Gutsche et. al., J. Am.-Chem. Soc. 103, 3782 (1981); B. Dhawan et. al., J. Org. Chem. 48, 1536 (1983), U.S. Pat. No. 4,098,717 Buriks et. al., and European Patent Publication No. 0,309,291 (Application No. 88 308 897.3) the appropriate disclosures of which are incorporated herein by reference.

Calixarene and oxacalixarene derivatives may usefully be polymerbound by methods described in U.S. Pat. No. 4,642,362 Harris et. al., or 4,699,966 Harris et. al., or by methods analogous to those described for crown ethers in U.S. Pat. No. 4,447,585 Parker or Tetrahedron 36 461-510 (1980). The derivatives may also be silica gel bound by methods analogous to those described in J. Incl. Phenomena 7 127-136 (1989) or J. Chem. Soc. Chem. Comm. 812 (1988).

DESCRIPTION OF THE PREFERRED EMBODIMENTS

The invention is illustrated in the following Examples:

EXAMPLE 1 a. Preparation

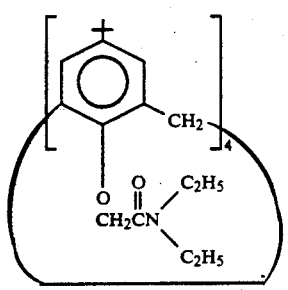

V

Tetramer starting material A (carboxylic acid) as described in European Patent Publication No. 0,237,265 (Application No. 87 301 900.4) was reacted with thionyl chloride to prepare starting Compound VI

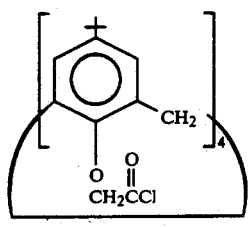

VI

To 2.38 g (0.0025 mole) of Compound VI in 10 mls. dry THF was added 2.19 g (0.03 mole) diethylamine and 3.03 g (0.03 mole) triethylamine at RT (room temperature); a white solid formed. The reaction mixture was stirred at RT for 24 hours, then all volatiles were removed and the entire was poured into water to give a white precipitate product which was filtered off and dried at 120° C. overnight; wt=2.7 g (100%). Recrystallation from heptane gave 2.2 g title Compound V; mp: 228°-31° C.

b. Preparation

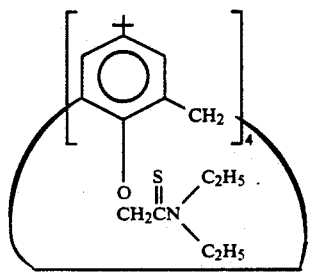

VII

To 2.7 g (0.0025 mole) of the product V of Example 1a in 10 mls dry HMPA was added 2.2 g (0.0054 mole) Lawesson's Reagent p-methoxyphenylthionophosphine sulphide dimer and the entire was stirred under dry $N_2$ following the method of S. Scheibye et. al., Bull Soc. Chem. Belg. 87 (3) 1978 p229 for 4 hours at 100° C. after which following cooling the reaction mixture was poured into ice water and the pale yellow-brown solid that formed was filtered off and taken up in 20 mls dichloromethane which was washed twice with water following drying with dried $MgSO_4$ to give after solvent removal 2.7 g crude solid. Chromatography on neutral alumina using dichloromethane as eluent gave 1.4 g high purity title Compound VII, pale yellow solid, mp 92°-4° C.

Elemental Analysis for $C_{68} H_{100} N_4 O_4 S_4$. Theory C=70.05., H=8.65; N=4.81; O=5.49; S=11.00; Found C=69.56; H=8.55; N=4.41; O=5.94; S=11.28.

Ion extraction

The ion binding abilities of calixarene and oxacalixarene derivatives were measured by extraction of metal picrates from aqueous into organic media. In the experiments a solution of the calixarene or oxacalixarene in dichloromethane was prepared at $2.5\times10^{-4}M$. Metal picrates were prepared as neutral aqueous $2.5\times10^{-4}M$ solutions (see Aggarwal et. al., Def. Sci. J., Vol. 25, October 1975, 153).

Equal volumes of each solution (5 millilitres) were shaken together for 3 minutes and the percentage extraction of metal picrate into organic phase was determined by measuring the increase in absorbance of dichloromethane layer at λm ca 355 nm (cupric and silver picrate) and λm 387 nm (sodium picrate) in a u.v. spectrophotometer.

The results are presented in the following table, comparing the ion binding ability of Compound VII with the amide derivative of formula V:

| Compound: | % Extraction Neutral Picrates | | | | | |
|---|---|---|---|---|---|---|
| VII | $Na^+$ | $K^+$ | $Ag^+$ | $Cu^{2+}$ | $Ca^{2+}$ | $Pb^{2+}$ |
|  | 7.44 | 8.58 | 80.30 | 19.08 | 1.90 | 55.70 |
|  | $Mg^{2+}$ | $Ba^{2+}$ | $Co^{2+}$ | $Cd^{2+}$ | $Pr^{3+}$ |  |
|  | 2.64 | 3.22 | 3.66 | 7.77 | 2.31 |  |
| V | $Na^+$ | $K^+$ | $Ag^+$ | $Cu^{2+}$ | $Ca^{2+}$ | $Pb^{2+}$ |
|  | 95.4 | 54.0 | 81.3 | 9.6 | 80.9 | 99.7 |

The sequestering ability of this thioamide functional calixarene tetramer VII and its advantage over the amide V is clearly seen from the above metal extraction data which show that Compound VII preferentially sequesters heavy/precious metals over alkaline earths and alkali metals.

EXAMPLE 2

Preparation

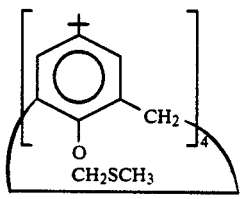

VIII 1.62 g (0.0025 mole) p-t-butylcalix-4-arene was reacted with 1.50 g (0.01 mole) dry sodium iodide, 0.72 g (0.03 mole) sodium hydride and 2.9 g (0.030 mole) chloromethyl methyl sulphide $ClCH_2SCH_3$ in 10 mls dry N-methylpyrrolidone under nitrogen at room temperature with stirring for 72 hours. After this period of time the reaction mixture was poured into 5% aqueous $H_2SO_4$ and the sticky buff coloured solid was then taken up in dichloromethane which was washed successively with 5% aqueous $H_2SO_4$ and then water after which the organic layer was dried with dried magnesium sulphate. Removal of volatiles, the last traces under reduced pressure, gave 2.0 g (90% yield) required product. Chromatography on neutral alumina using dichloromethane as eluent gave high purity off-white product VIII; mp 88°-91° C.

Elemental Analysis results: (Calculated for $C_{52}$ $H_{72}$ $O_4$ $S_4$ C=70.22; H=8.16, S=14.42; Found C=70.13; H=8.03, S=14.01).

Ion Extraction (as in Example 1) for Compound VIII

| $M^{n+}$ | Picrate % E |
|---|---|
| $Li^+$ | 0 |
| $Na^+$ | 0 |
| $K^+$ | 0 |
| $Mg^{2+}$ | 0 |
| $Ca^{2+}$ | 0 |
| $Ba^{2+}$ | 0 |
| $Y^{3+}$ | 2.06 |
| $Mn^{2+}$ | 0 |

-continued

| $M^{n+}$ | Picrate % E |
|---|---|
| $Fe^{2+}$ | 0 |
| $Co^{2+}$ | 0 |
| $Ni^{2+}$ | 0 |
| $Cu^{2+}$ | 0 |
| $Ag^+$ | 18.08 |
| $Au^{3+}$ | 5.71 |
| $Cd^{2+}$ | 0 |
| $Hg^{2+}$ | 6.41 |
| $Al^{3+}$ | 0 |
| $Pb^{2+}$ | 0 |
| $Ce^{3+}$ | 0 |
| $Gd^{3+}$ | 0 |
| $Yb^{3+}$ | 0 |

EXAMPLE 3

Preparation

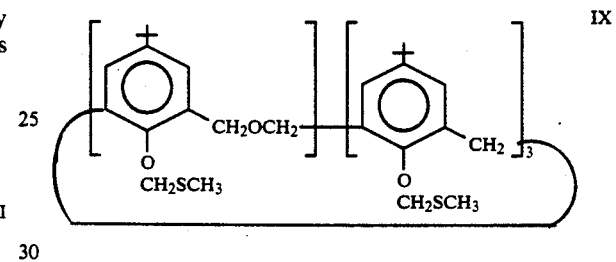

IX 1.69 g (0.0025 mole) p-t-butylpseudocalix-4-arene prepared following C.D. Gutsche et. al., J. Am. Chem Soc. 103 p3782 1981 was reacted with 1.5 g (0.01 mole) dry NaI, 0.72 g (0.03 mole) NaH and 2.9 gg (0.030 mole) chloromethylmethyl sulphide in 10 mls dry N M P under $N_2$ with stirring at RT for 72 hours. After this reaction time the reaction mixture was poured into 5% aqueous $H_2SO_4$ and the pale brown solid was taken up in 20 mls dichloromethane which was washed with 5% aqueous $H_2SO_4$ and then water and then dried with $MgSO_4$ to give after removal of solvent 1.9 g (88% yield) title Compound IX which was chromatographed on neutral alumina with $CH_2Cl_2$ to give pale yellow high purity product; mp 94° C.

Calculated for $C_{53}$ $H_{74}$ $O_5$ $S_4$ C=69.23; H=8.11; S=13.96

Found C=69.47; H=8.19, S=13.63

Ion Extraction (as in Example 1) for Compound IX

| $M^{n+}$ | Picrate % E |
|---|---|
| $Na^+$ | 0 |
| $K^+$ | 0 |
| $Cs^+$ | 0 |
| $Ca^{2+}$ | 4.86 |
| $Ba^{2+}$ | 0 |
| $Y^{3+}$ | 0 |
| $Fe^{2+}$ | 0 |
| $Ni^{2+}$ | 0 |
| $Cu^{2+}$ | 0 |
| $Ag^+$ | 31.72 |
| $Au^{3+}$ | 7.40 |
| $Zn^{2+}$ | 0 |
| $Hg^{2+}$ | 12.84 |
| $Pb^{2+}$ | 0 |
| $Ce^{3+}$ | 0 |
| $Nd^{3+}$ | 0 |
| $Pr^{3+}$ | 0 |
| $Gd^{3+}$ | 0 |
| $U^{4+}$ | 6.28 |

| -continued | |
|---|---|
| | Picrate |
| M$^{n+}$ | % E |
| Yb$^{3+}$ | 0 |

EXAMPLE 4 a. Preparation

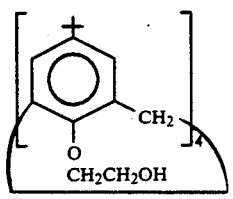

XV 1.0 g of the tetraethylacetate of p-t-butylcalix-4-arene prepared as in U.S. Pat. No. 4,556,700 S. Harris et. al., (0.001 mole) was dissolved in 50 mls dry toluene under nitrogen and to this was added with stirring 10.9 mls (0.016 mole) of a 25% Dibal-H (diisobutylaluminium hydride from Aldroxl) solution in toluene at room temperature. The reaction mixture was then stirred at room temperature for a further 72 hours, then methanol was added carefully to destroy excess Dibal-H. The gelatinous reaction mixture was then broken down by dropwise addition of water with gentle mixing. The solid aluminium hydroxide was removed by filtration through Celite and the precipitate washed well with dichloromethane. The filtrate was dried with dried magnesium sulphate and then volatiles were removed, the last traces at reduced pressure, to give 0.8 g (96% yield) colourless solid of title compound. Recrystallisation from ethanol afforded microanalytically pure title product XV, mp greater than 300° C.

b. Preparation

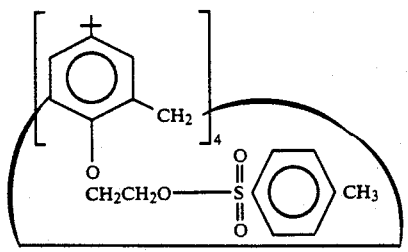

XVI 16.5 g of Compound XV from Example 4 (0.0199 mole) was dissolved in 90 mls dry pyridine in a glass stoppered Erlenmeyer flask cooled to 0° C. 22.8 g (0.119 mole) of p-toluenesulphonyl chloride was then added and the reaction mixture well shaken to effect dissolution. The resulting orange solution was placed in a 0° C. fridge for 24 hours following which an identical quantity of p-toluene-sulphonylchloride was added. The flask was then left at 0° C. for a further 72 hours after which the solution containing long needles of pyridinium hydrochloride was poured into 300 mls ice/water. The resulting cloudy solution was stored for 1 hour following which a white sticky solid precipitated which was filtered off and stored in ethanol until a fine colourless solid precipitated which was filtered off to give 27.7 g (96% yield) of title product XVI mp 102°–4° C.

Elemental Analysis results: (Calculated for C$_{80}$, H$_{96}$, O$_{16}$, S$_4$, C=66.66; H=6.66, S=8.88; Found C=66.79, H=6.88; S=8.54).

c. Preparation

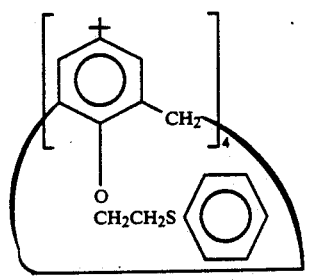

X 10 g (0.0069 moles) of the tosylate Compound XVI prepared as in Example 4b in 20 g toluene was added dropwise during 30 minutes under N$_2$ with stirring to 200 g absolute ethanol to which had been added 1.27 g sodium metal (0.055 mole) until completely reacted (dissolved) and thence had been added 6.1 g (0.055 mole) thiophenol at room temperature. After completion of addition the reaction mixture was stirred at 60°–70° C. for 72 hours under nitrogen. After this period of time all volatiles were removed under reduced pressure and the residual oil was taken up into 75 mls ether which was then washed with 10% aqueous NaOH and then water. The ether layer was then dried over dried magnesium sulphate and the volatiles removed to give 8.2 g (approx. 100% yield) off-white solid product which was recrystallised from ethanol to give 4.7 g (57% yield) pure colourless crystalline product identified as title product X; mp 92°–95° C.

Elemental Analysis for C$_{76}$ H$_{88}$ O$_4$ S$_4$ Theory C=76.51; H 7.38; S 10.74; Found C=76.87; H 7.41; S 10.40%.

Ion Extraction (as in Example 1) for Compound X

| M$^{n+}$ | Li$^+$ | Na$^+$ | Rb$^+$ | Cs$^+$ | Ca$^{2+}$ | Ag$^+$ | Cu$^{2+}$ | Pb$^{2+}$ |
|---|---|---|---|---|---|---|---|---|
| % E | 0 | 0 | 0 | 0 | 0 | 4.8 | 0 | 0 |

EXAMPLE 5

Preparation

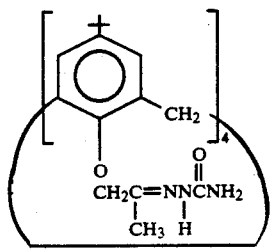

XI (semicarbazone)

To 0.5 g of Compound XII

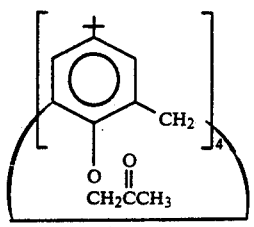

XI prepared according to European Patent Publication No. 0,262,910 (Application No. 87 308 585.6) was added 1 g of semicarbazide hydrochloride following the method described in Vogel's Textbook of Practical Organic Chemistry, 4th Edition, Revised by B.S. Furniss, A.J. Hannaford, V. Rogers, P.W.G. Smith and A.R. Tatchell, Longman N.Y. 1981 p1112, and 1.5 g of crystallised sodium acetate in 10 ml water and 20 mls absolute ethanol, and the entire was then refluxed for 20 minutes after which time a clear solution resulted. After cooling, volatiles were removed and the off-white solid residue was washed with water and then was recrystallised from absolute alcohol to give 0.6 g colourless crystalline product (95%), mp 250°–252° C., characterised by infra-red spectroscopy and elemental analysis as title Compound XI.

i.r. spectroscopy results: $\nu$no C=O at 1720 cm$^{-1}$; from starting material, $\nu$3480 cm$^{-1}$(m), 3340 cm$^{-1}$(w), 3200 cm$^{-1}$NH, 1700(S) C=O, 1560-1580 cm$^{-1}$ m C=N.

Elemental Analysis results: (Calculated for $C_{60}$ $H_{84}$ $N_{12}$ $O_8$ C=65.43, H=7.69, N=15.26; Found C=65.01, H=7.90; N=14.76).

EXAMPLE 6

Preparation

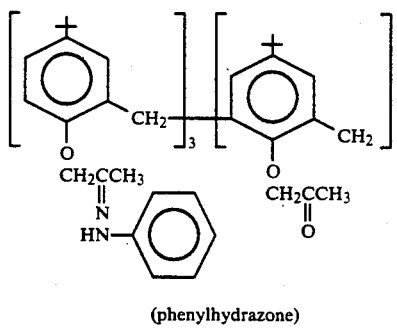

XIII (phenylhydrazone)

To 0.4 g Compound XII prepared as in Example 5 was added 10 ml absolute ethanol, 0.5 g phenylhydrazine hydrochloride and 0.8 g sodium acetate in 5 mls water following the method in Vogel (see Example 5 for reference). The entire was refluxed 17 for 30 minutes, then volatiles were removed to give 0.5 g (88%) product after washing well with water and drying. The yellow solid was recrystallised from absolute ethanol to give high purity title compound as pale yellow crystals, m.pt 114°–116° C., characterised by i.r. spectroscopy and elemental analysis as the title Compound XIII.

i.r spectroscopy results: 3350 cm$^{-1}$(m)NH 1735(m) C=O, 1600(m) C=N

Elemental Analysis results: (Calculated for $C_{74}$ $H_{90}$ $N_6$ $O_5$ C=77.72, H=7.93, N=7.35; Found C=75.31, H=8.13; N=7.58).

Ion extraction (as in Example 1)

| Compound | mp | % Extraction | | |
|---|---|---|---|---|
| | | Silver Picrate | Cupric Picrate | Sodium Picrate |
| XI | 250–252° C. | 7.1 | 0 | 0 |
| XIII | 114–116° C. | 9.3 | 9.4 | 2.8 |

EXAMPLE 7

Preparation (oxime)

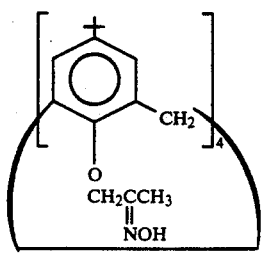

XIV 0.5 g compound XII prepared as in Example 5 was refluxed with 0.5 g hydroxylamine hydrochloride, 5 ml absolute ethanol and 0.5 ml pyridine following the procedure described in Vogel p1113 (see more details of reference in Example 5) for 2 hours, following which all volatiles were removed and the residual solid washed well with water to give 0.5 g (94%) product which was recrystallised from ethanol-water to give pure colourless crystalline product, mp 138°–9° C., characterised as title compound XIV by i.r. spectroscopy and elemental analysis.

i.r. spectroscopy results: $\nu$no peak at 1720 cm$^{-1}$ from starting material 3250 cm$^{-1}$(m) NOH Elemental Analysis results: (Calculated for Compound XIV.CH$_3$ CH$_2$ OH: $C_{58}$ $H_{82}$ $N_4$ $O_9$ C=71.13, H=8.44, N=5.72, O=14.70; Found C=68.54, H=8.08, N=5.31, O=14.37).

Ion Extraction (as in Example 1) for Compound XIV

| $M^{n+}$ | % E |
|---|---|
| $Yb^{3+}$ | 17.3 |
| $Gd^{3+}$ | 17.6 |
| $Eu^{3+}$ | — |
| $U^{4+}$ | 18.9 |
| $Zn^{2+}$ | 22.7 |
| $Cd^{2+}$ | 19.2 |
| $Hg^{2+}$ | 19.8 |
| $Pt^{4+}$ | 23.5 |
| $Au^{3+}$ | 23.6 |
| $Pb^{2+}$ | 37.0 |
| $Ca^{2+}$ | 18.0 |
| $Ba^{2+}$ | 22.0 |
| $Y^{3+}$ | 16.9 |
| $Li^+$ | 31.5 |
| $Na^+$ | 44.4 |
| $K^+$ | 35.1 |
| $Rb^+$ | 35.7 |
| $Cs^+$ | 32.1 |
| $Mg^{++}$ | 19.4 |
| $Mn^{2+}$ | 20.2 |
| $Fe^{2+}$ | 21.1 |
| $Co^{2+}$ | 23.2 |
| $Al^{3+}$ | 16.9 |
| $Ag^+$ | 76.0 |

-continued

| $M^{n+}$ | % E |
|---|---|
| $Cu^{2+}$ | 21.7 |

EXAMPLE 8 a. Preparation

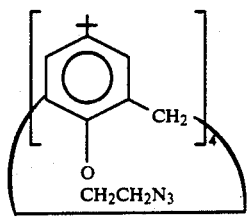

XVII 9.5 g (0.0066 mole) tosylate XVI from Example 4b was dissolved in 100 mls dry DMF to which was added with stirring under nitrogen 5.1 g (0.079 mole) sodium azide. The reaction mixture was stirred at room temperature for 168 hours and then 100 mls water was added. The resulting solution was extracted with 3×100 mls diethyl ether, the combined organic extract then washed with 2×100 mls aqueous sodium chloride and the ether layer was then dried with dried magnesium sulphate and the volatiles were then removed, the last traces at reduced pressure, to give 5.9 g (97% yield) off-white product. Recrystallisation from ethanol gave pure title compound XVII, mp 197°–9° C.

Elemental Analysis results: (Calculated for $C_{52}H_{68}N_{12}O_4$; C=67.51, H=7.41, N=18.16; Found C=67.65, H=7.54, N=17.95).

b. Preparation

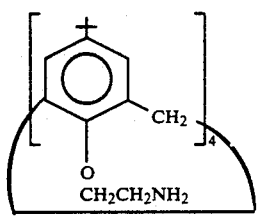

XVIII 1 g (0.001 mole) azide from Example 8a was dissolved in 40 mls dry toluene to which was added with stirring under nitrogen 10.8 ml (0.016 mole) 25% Dibal-H in toluene. The reaction mixture was stirred at room temperature for a further 24 hours and then excess Dibal-H was destroyed by careful addition of methanol. The gelatinous reaction mixture was broken down by addition of water. The aluminium hydroxide precipitate was then filtered off through Celite and this was washed with dichloromethane. The combined filtrates were dried over dried magnesium sulphate and solvent removed, the last traces at reduced pressure, to give 0.79 g (96% yield) of pale yellow title product XVIII; mp 110°–114° C.

Ion Extraction (as in Example 1) for Compound XVIII

| $M^{n+}$ | % E |
|---|---|
| $Yb^{3+}$ | 28.9 |
| $Gd^{3+}$ | 31.7 |
| $Eu^{3+}$* | 40.6 |
| $U^{4+}$ | 28.5 |
| $Zn^{2+}$ | 11.8 |
| $Cd^{2+}$ | 40.5 |
| $Hg^{2+}$ | 66.3 |
| $Pt^{4+}$ | 26.0 |
| $Au^{3+}$ | 44.9 |
| $Pb^{2+}$ | 49.8 |
| $Ca^{2+}$ | 46.3 |
| $Ba^{2+}$ | 43.0 |
| $Mg^{2+}$ | 46.2 |
| $Mn^{2+}$ | 49.5 |
| $Li^+$ | 83.1 |
| $Na^+$ | 93.1 |
| $K^+$ | 85.4 |
| $Al^{3+}$ | 39.8 |
| $Fe^{2+}$ | 51.6 |
| $Co^{2+}$ | 42.1 |
| $Cu^{2+}$ | 55.0 |
| $Cs^+$ | 82.6 |
| $Ag^+$ | 92.2 |
| $Rb^+$ | 84.6 |

*measured in $ClCH_2CH_2Cl$

EXAMPLE 9 a. Preparation

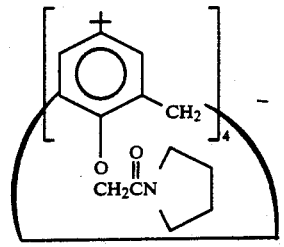

XX

To 2.38 g (0.0025 mole) of Compound VI (prepared as in Example 1) in 10 mls. dry THF was added 2.13 g (0.03 mole) pyrrolidine and 3.03 g (0.03 mole) triethylamine at RT (room temperature); a white solid formed. The reaction mixture was stirred at RT for 24 hours, then all volatiles were removed and the entire was poured into water to give a white precipitate product which was filtered off and dried at 120° C. overnight; wt=2.6 g (100%). Recrystallation from heptane gave 2.2 g title Compound; mp: 232°–4° C.

Elemental Analysis Calculated for $C_{68}H_{92}O_8N_4$ C=74.69, H=8.48, N=5.12, O=11.70; Found C=74.71, H=8.21, N=5.01, O=11.11%.

b. Preparation

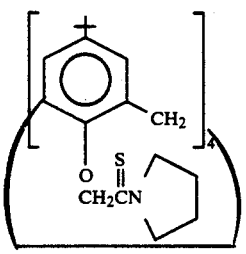

XXI

To 2.7 g (0.0025 mole) of Compound XX in 10 mls. dry HMPA was added 2.2 g (0.0054 mole) Lawesson's Reagent p-methoxyphenylthionophosphine sulphide dimer and the procedure described in Example 1b was followed to give after solvent removal 2.7 g crude solid. Chromatography on neutral alumina using dichloromethane as eluent gave 1.4 g high purity title Compound XXI, pale yellow solid, which was recrystallised twice from methanol/$CH_2Cl_2$ to give pale yellow crystalline product mp 286°-7° C.

Elemental Analysis for $C_{68} H_{92} N_4 O_4 S_4$: Theory C=70.54; H=8.01; N=4.84; S=11.08; Found C=70.58; H=7.95; N=4.84; S=11.08.

Ion Extraction (as in Example 1) for Compounds XX and XXI

| $M^{n+}$ | XX-% E | XXI-% E |
|---|---|---|
| $Li^+$ | 50.00 | — |
| $Na^+$ | 100.00 | 3.60 |
| $K^+$ | 60.00 | 6.20 |
| $Rb^+$ | 16.00 | — |
| $Cs^+$ | 11.00 | — |
| $Mg^{2+}$ | 10.26 | 2.80 |
| $Ca^{2+}$ | 100.00 | — |
| $Ba^{2+}$ | 71.67 | 1.70 |
| $Sr^{2+}$ | 72.00 | — |
| $Y^{3+}$ | 10.86 | — |
| $Mn^{2+}$ | 23.53 | — |
| $Fe^{2+}$ | 18.00 | — |
| $Co^{2+}$ | 23.53 | 3.70 |
| $Ni^{2+}$ | 16.40 | — |
| $Pt^{4+}$ | 22.20 | — |
| $Cu^{2+}$ | 18.26 | 47.35 |
| $Ag^+$ | 100.00 | 97.70 |
| $Au^{3+}$ | 59.40 | — |
| $Zn^{2+}$ | 20.70 | — |
| $Cd^{2+}$ | 93.73 | 9.10 |
| $Hg^{2+}$ | 66.60 | — |
| $Al^{3+}$ | 13.53 | — |
| $Pb^{2+}$ | 100.00 | 96.10 |
| $Ce^{3+}$ | 8.87 | — |
| $Pr^{3+}$ | 10.41 | 2.90 |
| $Nd^{3+}$ | 11.85 | — |
| $Sm^{3+}$ | 12.17 | — |
| $Eu^{3+}$ * | 34.00 | — |
| $Gd^{3+}$ | 13.02 | — |
| $Yb^{3+}$ | 18.38 | — |
| $U^{4+}$ | 36.50 | — |

*Measured in $ClCH_2CH_2Cl$

EXAMPLE 10

Preparation

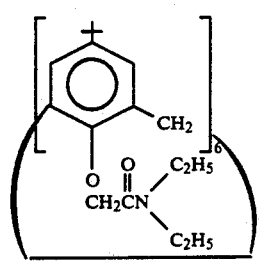

XXII

The hexaethylacetate of p-t-butylcalix-6-arene was prepared following the procedure given in U.S. Pat. No. 4,636,539 S.J. Harris et al assigned to Loctite (Ireland) Limited. This hexamer starting material was converted to its carboxylic acid derivative by hydrolysis with KOH in ethanol/water following the procedure given in European Patent Publication No. 0,237,265 (Application No. 87301900.4), and the carboxylic acid derivative was then converted to its acid chloride derivative by 2 hour reflux in thionyl chloride.

2.73 ml (0.026 mole) diethylamine and 2.94 ml (0.021 mole) triethylamine were dissolved in 25 mls. dry THF under $N_2$. To the well stirred solution at RT was added 4.2 g of the acid chloride derivative above (0.0 029 mole) in 25 mls. dry THF during 15 minutes. The entire was then allowed to stir at RT for 17 hours. All volatiles were then removed and the residue was taken up in 30 mls. dichloromethane which was then washed well with water which was then dried with dried magnesium sulphate. Removal of all volatiles gave 2.8 g (100%) crude pale yellow solid title product Recrystallisation from methanol/dichloromethane gave colourless crystalline product Compound XXII mp. 232° C. (d) (28% yield).

Elemental Analysis Calculated for $C_{102} H_{150} O_{12} N_6$; C=74.14, H=9.15, N=5.09; Found C=73.65, H=9.09, N=4.84.

Preparation

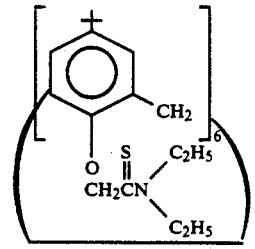

XXIII 1.5 g (0.00093 mole) Compound XXII in 10 mls. dry HMPA was added to 1.3 g (0.0032 mole) Lawesson's Reagent and the procedure described in Example 1b was followed to give after solvent removal 1.5 g crude solid. Chromatography on neutral alumina using dichloromethane as eluent gave 0.8 g high purity title compound XXIII as a pale yellow solid mp 127° C. (d).

Elemental Analysis Calculated for $C_{102} H_{150} N_6 O_6 S_6 \cdot CH_2Cl_2$ C=67.46, H=8.36, N=4.58; Found C=67.51, H=8.37, N=4.23.

Ion Extraction (as in Example 1) for Compound XXIII

| $M^{n+}$ | XXII-% E | XXIII-% E |
|---|---|---|
| $Li^+$ | 31.2 | 12.21 |
| $Na^+$ | 29.8 | 7.50 |
| $K^+$ | 32.1 | 10.31 |
| $Rb^+$ | 28.3 | 15.40 |
| $Cs^+$ | 34.0 | 12.80 |
| $Mg^{2+}$ | — | 3.10 |
| $Ca^{2+}$ | 94.6 | 6.40 |
| $Ba^{2+}$ | 94.6 | 9.70 |
| $Y^{3+}$ | — | — |
| $Mn^{2+}$ | 21.7 | 4.30 |
| $Fe^{2+}$ | 10.2 | 5.10 |
| $Co^{2+}$ | 9.7 | 4.60 |
| $Ni^{2+}$ | 18.9 | 6.02 |
| $Pt^{4+}$ | 31.4 | — |
| $Cu^{2+}$ | — | 9.70 |
| $Ag^+$ | 52.5 | 94.4 |
| $Au^{3+}$ | — | — |
| $Zn^{2+}$ | 22.1 | 7.50 |
| $Cd^{2+}$ | 43.8 | 10.40 |
| $Hg^{2+}$ | — | — |
| $Al^{3+}$ | 7.8 | 3.60 |
| $Pb^{2+}$ | 94.6 | 45.60 |
| $Ce^{3+}$ | — | — |
| $Pr^{3+}$ | — | 4.60 |
| $Sm^{3+}$ | — | 7.55 |
| $Nd^{3+}$ | 21.0 | 7.18 |
| $Gd^{3+}$ | 30.8 | 7.15 |
| $Yb^{3+}$ | 18.8 | 4.30 |
| $U^{4+}$ | — | — |

EXAMPLE 11 a. Preparation

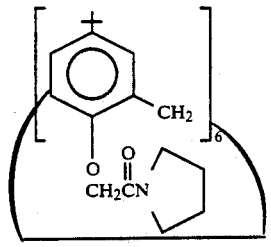

XXIV

The hexaethylacetate of p-t-butylcalix-6-arene was prepared following the procedure given in U.S. Pat. No. 4,636,539 S.J. Harris et al assigned to Loctite (Ireland) Limited. This compound was converted to its carboxylic acid derivative which was then converted to its acid chloride derivative by the procedure described in Example 10.

5.2 mls. of pyrrolidine (0.062 mole) and 4.8 mls. (0.059 mole) of pyridine were dissolved in 30 mls. dry THF under $N_2$. To the well stirred solution was added 2.5 g (0.00175 mole) of the hexa acid chloride prepared as described above in 15 mls. dry THF during 15 minutes at RT. The reaction mixture was then stirred under $N_2$ for 17 hours at RT.

All volatiles were then removed and the residue was taken up in 30 mls. dichloromethane which was then washed well with water, then dried over dried magnesium sulphate. Removal of volatiles gave 2.8 g (100%) crude pale yellow solid title product Compound XXIV. Recrystallisation from methanol/dichloromethane furnished colourless crystalline product mp 305° C. (250° C. starts to decompose) (yield 25%).

Elemental Analysis Calculated for $C_{102} H_{138} O_{12} N_6$; C=74.69, H=8.48, N=5.12; Found C=74.72, H=8.69, N=5.03.

b. Preparation

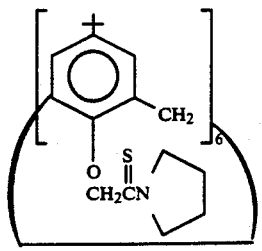

XXV 1.5 g (0.00093 mole) Compound XXIV in 10 mls. dry HMPA was added to 1.3 g (0.0032 mole) Lawesson's Reagent and the procedure described in Example 1b was followed to give after solvent removal 1.5 g crude solid. Chromatography on neutral alumina using dichloromethane as eluent gave 0.8 g high purity title compound XXV as a pale yellow solid. The melting point is greater than 320° C. The product starts to decompose at 230° C.

Elemental Analysis Calculated for $C_{102} H_{138} N_6 O_6 S_6 \cdot 2CH_2Cl_2$ C=68.05, H=7.80, N=4.57; Found C=66.80, H=7.50, N=3.96.

Ion Extraction (as in Example 1) for Compounds XXIV and XXV

| $M^{n+}$ | XXIV-% E | XXV-% E |
|---|---|---|
| $Li^+$ | 62.79 | 5.16 |
| $Na^+$ | 49.28 | 4.57 |
| $K^+$ | 55.44 | 4.96 |
| $Rb^+$ | 39.03 | 5.18 |
| $Cs^+$ | 46.39 | 5.79 |
| $Mg^{2+}$ | 14.81 | — |
| $Ca^{2+}$ | 39.73 | 2.54 |
| $Ba^{2+}$ | 39.16 | 2.80 |
| $Y^{3+}$ | 22.17 | — |
| $Mn^{2+}$ | 33.44 | 3.01 |
| $Fe^{2+}$ | 23.21 | 2.72 |
| $Co^{2+}$ | 21.25 | 3.43 |
| $Ni^{2+}$ | 37.10 | 2.98 |
| $Pt^{4+}$ | 18.91 | 40.94 |
| $Cu^{2+}$ | 30.94 | 41.60 |
| $Ag^+$ | 68.12 | 94.40 |
| $Au^{3+}$ | 26.40 | — |
| $Zn^{2+}$ | 32.06 | 3.28 |
| $Cd^{2+}$ | 36.87 | 57.90 |
| $Hg^{2+}$ | 36.07 | — |
| $Al^{3+}$ | 12.81 | 2.16 |
| $Pb^{2+}$ | 39.44 | 71.45 |
| $Ce^{3+}$ | 22.18 | — |
| $Sm^{3+}$ | 21.67 | — |
| $Gd^{3+}$ | 21.73 | 2.14 |
| $Yb^{3+}$ | 21.89 | — |
| $U^{4+}$ | 18.63 | — |

These results show that the thioamide hexamer XXV has an advantage over the amide XXIV in that it selectively sequesters silver and lead over alkaline earths and alkali metals.

We claim:

1. Calixarene and oxacalixarene derivatives of the formula IV;

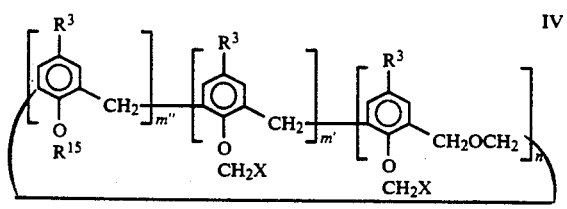

IV wherein (m'+mΔ)=0-8; n=0-8; m'≧½(m'+m"); and
3≦(m'+m"+n)≦8;
if n=0, then (m'+m")≧4; provided that m' and n cannot equal zero at the same time;
R³ is H, halogen, or a C₁-C₁₀ hydrocarbyl or C₆-C₂₀ aryl hydrocarbylaryl group, any of which may be substituted by one or more halo or oxo groups or interrupted by one or more oxo groups, and R³ may be the same or different on each aryl group;
R¹⁵ is H or a C₁-C₁₀ hydrocarbyl or C₆-C₂₀ aryl or hydrocarbylaryl group, any of which may be substituted by one or more halo or oxo groups or interrupted by one or more oxo groups; and
X is selected from the group consisting of

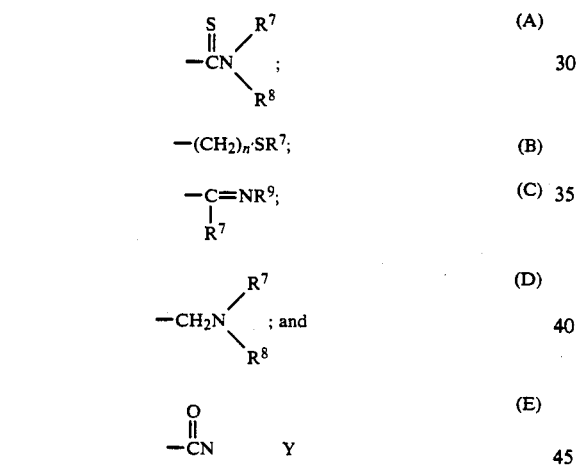

wherein R⁷ and R⁸, which may be the same or different, are H or a C₁-C₁₀ hydrocarbyl, including a cycloaliphatic ring formed by R⁷ and R⁸ together, or C₆-C₂₀ aryl or hydrocarbylaryl group, any of which may be substituted by one or more halo or oxo groups or interrupted by one or more oxo groups;
R⁹ is —OH, —NH₂, —NHC(O)NH₂ or —NHAr, wherein Ar is a C₆-C₂₀ aryl group which may be substituted with one or more halo or oxo groups or interrupted by one or more oxo groups; Y is a cycloaliphatic ring; and n' is 0 or 1.

2. Compounds according to claim 1 wherein m"=0.
3. Compounds according to claim 2 wherein n=0.
4. Compounds according to claim 1 wherein R⁹ is —OH, —NHC(O)NH₂ or —NHC₆H₅.
5. Compounds according to claim 1 wherein R³ is a hydrocarbyl group containing from 1 to 5 carbon atoms and R⁷ and R⁸ are each H, a hydrocarbyl group containing from 1 to 5 carbon atoms, or an aryl or hydrocarbylaryl group having from 6 to 10 carbon atoms.

6. Compounds according to claim 1 wherein R⁷ and R⁸ are each H or a hydrocarbyl group containing from 1 to 5 carbon atoms.
7. Compounds according to claim 1 wherein R⁷ and R⁸ together form a cycloaliphatic ring.
8. Calixarene compounds selected from the group of compounds consisting of the formulae:

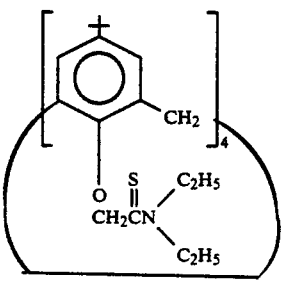

VII

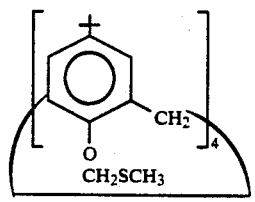

VIII

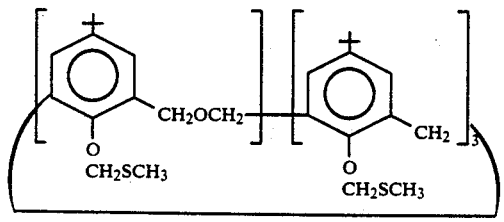

IX

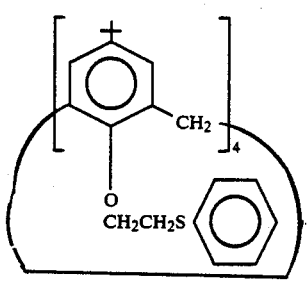

X

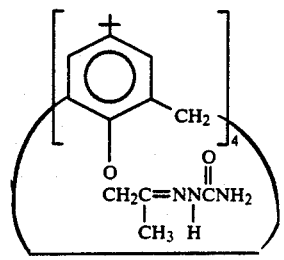

XI

-continued
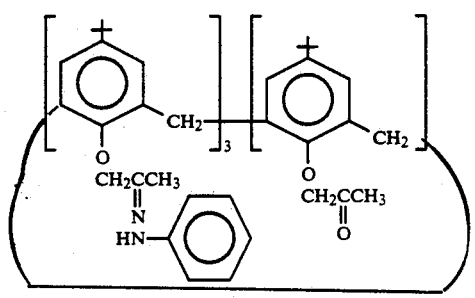 XIII
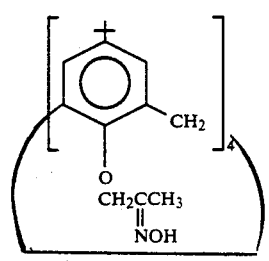 XIV
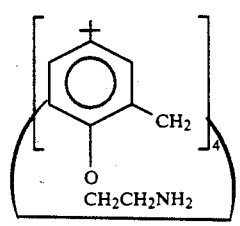 XVIII
-continued
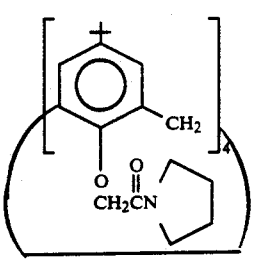 XX
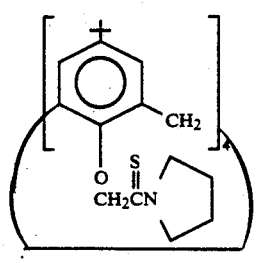 XXI
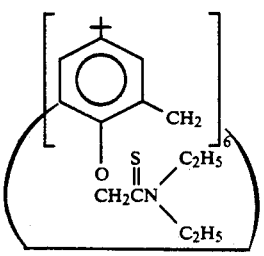 XXIII
and
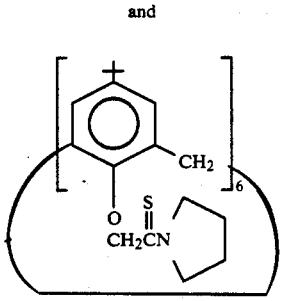 XXV
* * * * *